United States Patent [19]

Aretz et al.

[11] Patent Number: 5,316,929
[45] Date of Patent: May 31, 1994

[54] PROCESS FOR THE PREPARATION OF MA

[75] Inventors: Werner Aretz, Königstein/Taunus; Eberhard Ehlers, Hofheim am Taunus; Udo Hedtmann, Frankfurt am Main, all of Fed. Rep. of Germany

[73] Assignee: Hoechst Aktiengesellschaft, Frankfurt am Main, Fed. Rep. of Germany

[21] Appl. No.: 104,598

[22] Filed: Aug. 11, 1993

Related U.S. Application Data

[63] Continuation-in-part of Ser. No. 846,073, Mar. 5, 1992.

[30] Foreign Application Priority Data

Mar. 8, 1991 [DE] Fed. Rep. of Germany ........ 4107460

[51] Int. Cl.$^5$ .................... C12P 7/42; C07C 59/60; C12N 9/16
[52] U.S. Cl. ................................ 435/146; 435/196; 435/252.5
[58] Field of Search .................. 435/146, 196, 252.5

[56] References Cited

U.S. PATENT DOCUMENTS 3,660,569  5/1972  Schacht et al. .................... 424/124

FOREIGN PATENT DOCUMENTS 0355679  2/1990  European Pat. Off. ...... C07H 13/12

OTHER PUBLICATIONS

G. Huber, "Moenomycin and Related Phosphorus-Containing Antibiotics," *Antibiotics,* 1, 1979, pp. 135-153.

*Primary Examiner*—Herbert J. Lilling
*Attorney, Agent, or Firm*—Finnegan, Henderson, Farabow, Garrett & Dunner

[57] ABSTRACT

The invention relates to a process for the preparation of MA, which ensures MA production by enzymatic catalysis in glycine/NaOH buffer, and by the use of a phosphate-containing culture medium for Bacillus sp. DSM 4675 and by extraction of the biomass with acetone.

12 Claims, 2 Drawing Sheets

PROCESS FOR THE PREPARATION OF MA

This application is a continuation-in-part of application Ser. No. 07/846,073, filed Mar. 5, 1992.

DESCRIPTION

Moenomycin A is the main component of Flavomycin ® which is used in livestock nutrition. Like other known phosphoglycolipid antibiotics, it inhibits the biosynthesis of the peptidoglycan framework of the bacterial cell wall. More detailed investigations have found that the transglycosylation reaction of the penicillin-binding protein 1b of E. coli is inhibited by these substances [Huber G., Antibiotics, V-1, pp. 135-153, (1979)]. Attempts at specific enzymatic or microbial degradation of phosphoglycolipid antibiotics initially failed.

European Application EP 0 355 679 describes a process for the degradation of moenomycins (=phosphoglycolipid antibiotic) to MA, MB and MC catalyzed by the enzymes moenomycinase and MBase from Bacillus sp. DSM 4675.

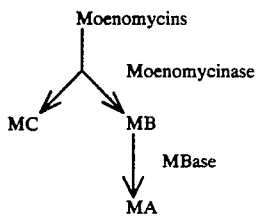

Examples of antibiotics in the moenomycin group are pholipomycin[1]), the prasinomycins[2]), the diumycins (macarbomycins)[3] esanchomycin, prenomycin and teichimycin, and other structurally related substances which have a corresponding functionalized phosphoglyceric acid

[1) S. Takahashi et al., Tetrahedron Lett. 1983, 499
2) F. L. Weisenborn et al., Nature 213, 1092 (1967)
3) S. Takahashi et al., J. Antibiot. 26, 542 (1973)].

In addition, EP 0 355 679 describes the aerobic fermentation of Bacillus spec. DSM 4675, the cleavage products resulting from the degradation of the moenomycins, the enzymes catalyzing the degradation, and the use of the degradation products as synthetic building blocks for the preparation of transglycosylase inhibitors (MA) or as substance with antibiotic activity (MB).

The process in the abovementioned application gives a 1% yield of MA because it is directed at the biologically active, i.e. antibiotically active, MB.

However, there is a distinct need to optimize processes for the preparation of MA because MA is a valuable building block for novel MA analogs, i.e. for novel transglycosylase inhibitors.

The invention thus relates to:
1. A process for the preparation of MA of the formula I

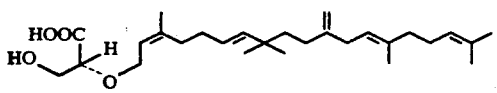

by enzymatic degradation of phosphoglycolipids, wherein the enzymatic catalysis takes place in a glycine/NaOH buffer.

2. A process as claimed in claim 1, wherein the culture medium for Bacillus sp. DSM 4675 is optimized with respect to the titers of moenomycinase and MBase by addition of phosphate.
3. A process as claimed in claim 1, wherein acid or alkaline phosphatase is employed as substitute for the enzyme MBase.
4. A process as claimed in claim 1, wherein the filtrate of the biomass is extracted with ethyl acetate and then with acetone, and the biomass itself is extracted by stirring with acetone.

Partially purified moenomycinase was dialyzed for 24 hours. The dialyzed moenomycinase was incubated with moenomycin A (6 mg/ml) in 100 mM potassium phosphate buffer, pH 8.0, for 31 hours with the addition of metal ions (0.5 or 1.0 mM, except $K^+=20$ mM0 or EDTA (10 mM). Enzyme activity was measured by determining the amount of MC formed using TLC and UV analysis as described in Example 3. The TLC plates were scanned at a wavelength of 254 nm using a DESAGA Chromatogram Densitometer CD50. Enzyme activity is expressed relative to the activity of the dialyzed preparation ("Dial").

Figure 1:
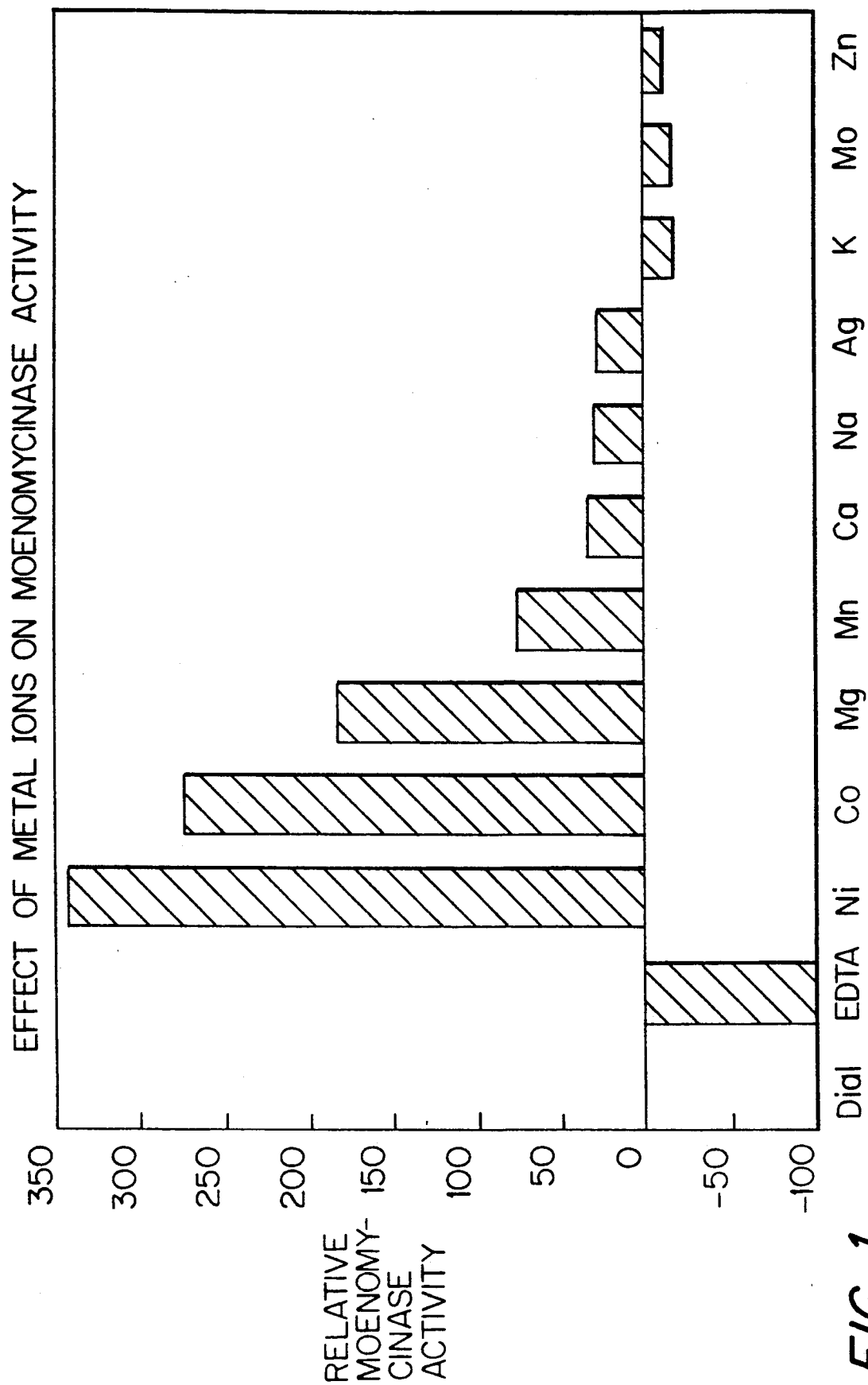
FIG. 1. Effect of Metal Ions on Moenomycinase Activity
Figure 2:
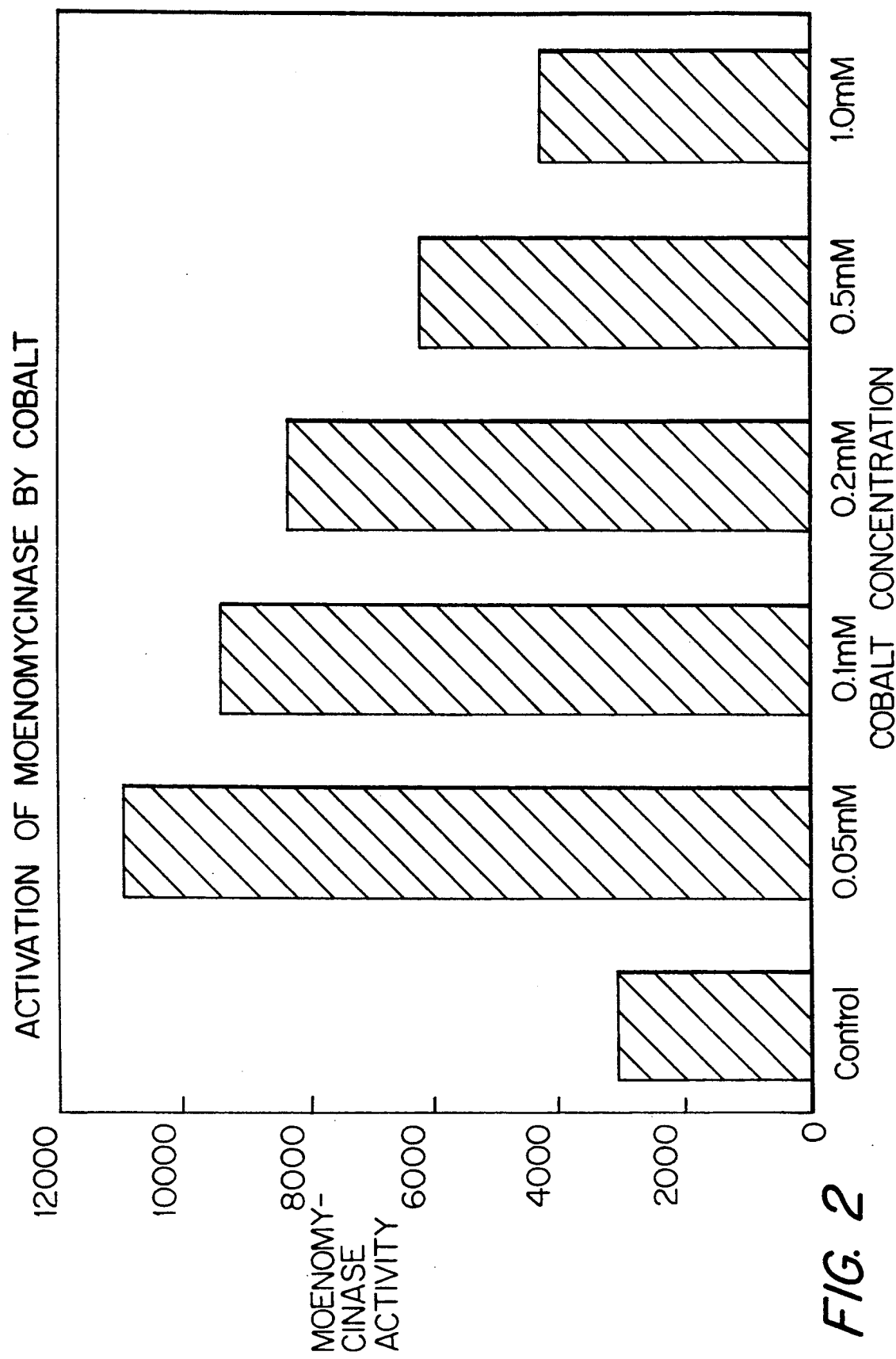

FIG. 2. Activation of Moenomycinase by Cobalt. Purified moenomycinase was incubated with moenomycin A in the presence of the indicated concentrations of $Co^{++}$. Enzyme activity was measured by determining the amount of MB formed using TLC and UV analysis as described in FIG. 1.

The invention is described in detail hereinafter, especially in the preferred embodiments. It is furthermore defined in the claims.

Unless otherwise indicated, percentage data relate to weight.

Bacillus sp. was deposited with the number DSM 4675 under the conditions of the Budapest Treaty at the Deutsche Sammlung von Mikroorganismen und Zellkulturen GmbH in Braunschweig, Germany, on June 23, 1988.

The growth of the microorganism Bacillus sp. DSM 4675 and the production of the enzymes necessary for the degradation reactions according to the invention is particularly good in a nutrient medium with the main components: citric acid, sodium gluconate, glycerol, peptone, phosphate and a vitamin solution. The concentration of the phosphate, for example potassium phosphate, is preferably 50-100 mM. The nutrient medium can, however, also be employed without phosphate or with phosphate in any desired physiological concentration. The content of gluconic acid or salt thereof is 1-2%, preferably 2%.

The fermentation is carried out aerobically, that is to say, for example, submerged with shaking or stirring in shaken flasks or fermenters, where appropriate introducing air or oxygen. The fermentation can be carried out in a temperature range from about room temperature to 50° C., preferably at about 35° to 37° C. The culture time is generally 8 to 48 hours, preferably 16-18 hours.

As described in EP 0 355 679, when Bacillus cells are used it is advantageous for them to be permeabilized, for example with cetyltrimethylammonium salts, or to be lyophilized. It is likewise possible to operate with protein isolates from the Bacillus cells or with enzyme extracts which have been partially concentrated by salting out or chromatography, or naturally with the purified enzyme. It is furthermore possible to employ the enzyme in free or immobilized form.

Lyophilized cells are preferably employed as source of enzyme for the enzymatic cleavage of the moenomycins to MA in the process according to the invention.

It is evident from the diagram on page 1 that two enzymes are necessary for the preparation of MA. One enzyme is needed for the cleavage of the phosphoglycosidic linkage of moenomycin A, and this was called moenomycinase by the inventors. Moenomycinase is associated with the cytoplasmic membrane of Bacillus sp. DSM 4675 and can be obtained from the microorganism by methods known per se for enzyme isolation.

For example, moenomycinase bound to membranes of Bacillus spec. DSM 4675 can be solubilized with the detergent Trion X-100 (1–3%) as described in Example 2A. Moenomycinase can also be isolated without the use of detergent by more extensive ultrasound sonication. For example, cells suspended in buffer (20 mM potassium phosphate, pH 8.0, with 0.1 mM $CICl_2$) were sonicated for 1–2 minutes. After centrifugration at 20 min×20,000 g, 50–60% of the enzyme activity was found in the supernatant. Alternatively, some activity can be solubilized with cetyltrimethylammonium salts. For example, when cells were incubated (1 g/2 ml) in 0.1% cetyltrimethylammonium salts (0.1%), 10% of the enzyme activity was found in the supernatant after centrifugation for 20 min×20,000 g.

The molecular weight of moenomycinase is 230,000±10,000 Dalton. Moenomycinase has an optical pH of 8.0 to 8.5 and an optimal temperature of 45° to 55° C. Moenomycinase has a $K_m$ value of 4 to 10 mmolar based on moenomycin A as substrate. Moenomycinase is activated by $Co^{++}$, $Ni^{++}$, $Ca^{++}$ and $Mg^{++}$ (0.05–1.0 mM0, and can be inhibited by formalin, EDTA, Cephalosporin C, and 7-aminocephalosporin acid (7-ACA). FIG. 1 illustrates the effects of metal ions and EDTA on moenomycinase activity. Although greatest activation is seen with $Ni^{++}$, the currently preferred ion for activation of moenomycinase for commercial development is $Co^{++}$ (0.10 mM). FIG. 2 shows the effect of $Co^{++}$ concentration on moenomycinase activity.

MBase can likewise be isolated from the microorganism by known methods. For example, the cells are disrupted with ultrasound, and the resulting crude extract is further concentrated either by ammonium sulfate fractionation (25–55% saturation) or ultracentrifugation. This is followed by dialysis. The moenomycinase and MBase are separated by chromatography.

MBase cleaves the phospholipid linkage of MB to give MA. MBase has an optimal pH of greater than 5.7 and an optimal temperature of less than 37° C.

In the process according to the invention the enzymatic cleavage, i.e. the conversion of the moenomycins into MA, preferably takes place in one mixture (Example 2).

The cleavage of the moenomycins is carried out with lyophilized cells or enzyme isolates, but preferably with lyophilized cells.

The reaction takes place in glycine/NaOH buffer. The pH of the buffer is preferably pH 8.0–8.5, otherwise in the range pH 7.5–10. The reaction takes place at 34°–39° C., preferably at 37° C. The pH of the enzyme reaction is in the range pH 7.0–9.0, preferably 7.8. The reaction time is generally 5–48 hours, preferably about 24 hours. The substrate concentration ought to be in the range from 0.1 to 5%, preferably 1 to 2%.

It is still possible likewise to carry out the reaction at higher or lower temperatures or pH values than stated. However, the enzyme activity is then lower.

It is possible to employ for the degradation of MB to MA besides MBase, as described in EP 0 355 679, also phosphatase. Preferably used are the acid phosphatase from potatoes and the alkaline phosphatase from calf intestine. The enzymes are commercially available (Sigma). Both enzymes can be employed in immobilized and non-immobilized form.

The MA of the formula I obtained by the cleavage reaction is subsequently isolated and purified. This is carried out by extraction of the filtrate of the biomass or of the biomass itself with organic solvents. Preferably employed as solvent is acetone in a ratio of 0.2–1, preferably 0.3, by volume. The purification by chromatography takes place by using a petroleum ether/acetone or petroleum ether/ethyl acetate mixture as washing liquid. Methanol is employed as MA eluent.

The resulting reaction product MA can be used as synthetic building block for transglycosylase inhibitors.

The invention is described further by means of examples.

EXAMPLE 1

Maintenance of the Bacillus sp. DSM 4675 strain

The maintenance of the strain and the culturing of the preculture are described in European Patent Application 0 355 679 (Examples 1 and 2).

a) A 12 l laboratory fermenter containing 9 l of medium of the following composition serves as main culture stage:

| Peptone | 12.5 g/l |
|---|---|
| Glycerol | 20.0 g/l |
| Citrate | 2.0 g/l |
| Na gluconate | 10.0 g/l |
| $K_2HPO_4$ | 10.0 g/l |
| $MgSO_4 \times 7H_2O$ | 0.5 g/l |
| $FeCl_3 \times 6H_2O$ | 0.04 g/l |
| Vitamin solution | 1 ml |
| Vitamin solution: | |
| Nicotinic acid | 0.35 g/l |
| Thiamine HCl | 0.30 g/l |
| D-Biotin | 0.01 g/l |
| p-Aminobenzoic acid | 0.20 g/l |
| Pyridoxal HCl | 0.10 g/l |
| Ca pantothenate | 0.10 g/l |
| Vitamin B12 | 0.05 g/l |

This is incubated with 500 ml of preculture at 37° C., 300 rpm and an aeration rate of 0.5 vvm for 16–18 hours.

The fully grown culture is centrifuged and then lyophilized.

The novel medium and the shortened fermentation time result in a doubling of the biomass yield. The biomass is characterized by means of the optical density. The measured OD=7. In addition, the resulting cells degrade moenomycins to MA with a high yield.

In a test mixture with 100 μl of crude extract, 12 mg of moenomycin A and 900 μ of potassium phosphate buffer (pH 8.0) 50 mM, 50% of the substrate employed is degraded within 7-24 hours at 37° C. The reaction products found are MA, MB and MC.

b) If the medium described under a) is used but without the addition of phosphate there is a distinct reduction in biomass. The measured OD=3.

EXAMPLE 2

Conversion of the moenomycins into MA (enzymatic cleavage)

Lyophilized cells of Bacillus sp. DSM 4675 are used for the conversion.

a) 90-200 g of lyophilisate are suspended in 9 l of glycine/NaOH buffer, 100 mM, pH 8.5, and, after addition of 135 g of moenomycin mixture or after addition of MB, 1.8 g of Na azide and 214 mg of $CoCl_2$, incubated at 37° C. and 190 rpm for 6-48 hours.

The course of the reaction, which is followed by TLC analysis, shows that up to 80% of the substrate is degraded to MB and MA. Of the cleavage products, about 10-20% comprises MB and about 80-90% comprises MA.

This way of carrying out the reaction makes large-scale production of MA possible.

b) A yield of 60% MA is obtained when a buffer of identical composition but with pH 9.0 is employed.

c) The yield of MA is likewise reduced to 60% when a tris-HCl buffer [100 mM tris, pH 7.8, otherwise the composition corresponds to the buffer stated under a)] is used.

EXAMPLE 2A

Isolation of Moenomycinase

Moenomycinase has been isolated from Bacillus spec. DSM 4675 as follows:

Cells grown as in Example 2 were suspended at a concentration of 1 g cells/2 ml in 20 mM potassium phosphate buffer, pH 8.0, containing 0.1 mM $CoCl_2$. The suspended cells were sonicated for 20 seconds. After sonication, the suspension were centrifuged for 20 min×20,000 g. The supernatant was discarded and the pellet resuspended in the same buffer to which has been added 1% Triton X-100 and incubated for 1 hr at room temperature with stirring. The suspension was then centrifuged for 2.5 hrs ×100,000 g. After such centrifugation, 90-95% of the moenomycinase activity was found in the supernatant.

Moenomycinase solubilized using Triton X-100, as described above, was further purified by $(NH_4)_2SO_4$ precipitation. As $(NH_4)_2SO_4$ concentration was increased from 0% to 40%, the moenomycinase precipitated at 30-40% and entered a fatty phase that floats above the aqueous phase. The aqueous phase was discarded, and the fatty phase was dissolved in 20 mM Tris HCl buffer, pH 8.0, containing 0.1 mM $CoCl_2$ and 0.1% Triton X100.

The dissolved enzyme was further purified by chromatography. For anion exchange chromatography, the enzyme was bound to a column of DEAE-52 (Whatman) or MonoQHR-5-5 (Pharmacia) and then eluted with 0.1-1.0 M NaCl. Presence of moenomycinase in the fractions was monitored by measuring the conversion of moenomycin A to MC, as described in Example 3, below. Further purification was achieved using hydrophobic chromatography. The enzyme was bound to phenylsepharose (Pharmacia), and was then eluted with 40% methanol. The enzyme was concentrated by ultrafiltration using an ultrafiltration membrane (Millipore) which retains molecules with molecular weights $\geq$ 10,000 Dalton.

The moenomycinase was further purified by molecular sieve chromatography using a Sephacryl S-200HR (Pharmacia). The enzyme was separated in the Sephacryl chromatography column in 20 mM Tris HCl or potassium phosphate buffer, pH 8,0, containing 0.1 mM $CoCl_2$ and 0.1% Tirton X-100 and washed with additional buffer. By comparison with the elution profiles of a series of standard proteins of differing molecular weight, the molecular weight of the moenomycinase was determined to be 230,000±10,000 Dalton. If desired, the purity of the isolated moenomycinase fraction can be checked using SDS gel chromatography.

EXAMPLE 3

Enzymatic cleavage of MB using phosphatases

The use of acid phosphatase from potatoes and alkaline phosphatase from calf intestine for the preparation of MA from MB was investigated.

The conversion of MB (5 mg/ml) into MA is about 50% with acid phosphatase (10 U/ml of mixture) at pH 4.8 and room temperature, and more than 90% with alkaline phosphatase (50 U/ml) at pH 8.0 within 144 hours. The conversion rate of the alkaline phosphatase is distinctly increased (<24 h) in the presence of 0.1 mM $ZnCl_2$ and $MgCl_2$ at pH 10.5 (glycine/NaOH buffer, 100 mM) and 37° C.

It is likewise possible to use immobilized alkaline phosphatase. In this case 35 U/ml under the above-mentioned conditions convert more than 90% of the substrate within 28 h.

EXAMPLE 4

Isolation of the Flavomycin degradation product MA

The solids present in the suspension resulting from the enzymatic conversion are removed by centrifugation.

The resulting biomass is extracted by stirring several times with the same volume of acetone at room temperature until MA is no longer detectable in the organic phase by thin-layer chromatography. The MA-containing extracts are combined.

The filtrate obtained after removal of the biomass is initially extracted once with ⅓ of its volume of ethyl acetate. The aqueous-organic, colloidal solution is then extracted with ⅓ of its volume of acetone until MA is no longer detectable by TLC in the organic phase which can be separated off in each case.

The MA-containing extracts are combined with the acetone extracts of the biomass, and the solvent is removed in vacuo.

The Flavomycin component MB can be isolated from the remaining aqueous reaction solution by extraction several times with n-butanol. The crude MB obtained after removal of the solvent by distillation in vacuo can be used anew for the enzymatic reaction for preparing MA.

On average, about 110 g of crude MA and about 85 g of crude MB are obtained by the extraction process described above from about 500 g of the Flavomycin A/C complex.

EXAMPLE 5

Purification of MA by chromatography

The MA obtained after evaporation of the solvent is subsequently purified by column chromatography on silica gel.

For this, about 20 g of crude MA are dissolved in the minimum amounts of a 1:1 petroleum ether/acetone mixture and loaded under 7-10 bar at a flow rate of 5 1/h onto a steel column containing about 2.1 kg of silica gel 60 (pH =7.5) as stationary phase. Washing is then carried out with about 10 l of a petroleum ether/acetone (6:4) mixture under the same conditions. The washing liquid is collected in a single fraction. Elution is then carried out with about 5 l of pure methanol.

The methanol eluate is collected in fractions each of 0.1 l. The MA-active pure fractions detected by TLC are combined, and the solvent is removed in vacuo. MA is obtained as a pale yellow highly viscous oil. Marginal fractions can be rechromatographed. About 13 g of pure substance are obtained from about 20 g of crude MA.

Precoated silica gel plates are used for the detection of MA by thin-layer chromatography. The mobile phase used is a solvent mixture composed of chloroform/methanol/ acetic acid (80: 10: 1). Detection is effected by staining the developed plates with PMS and subsequently drying them at 130° C. Also applied as comparison substances are MA, MB and the Flavomycin A/C complex.

We claim:

1. A process for the preparation of the compound of the formula I

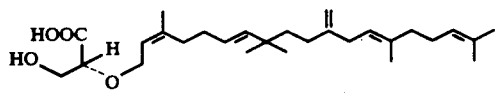

by enzymatic degradation of phosphoglycolipids in a glycine/NaOH buffer using moenomycinase and an enzyme selected from MBase and phosphatase, wherein moenomycinase has the following characteristics;
 (i) the ability to cleave phosphoglycolipid antibiotics at the phosphoglycosidic linkage;
 (ii) a pH optimum of 8.0 to 8.5;
 (iii) a temperature optimum of 45° to 55° C.;
 (iv) a $K_m$ value of 4 to 10 mmolar based on moenomycin A as substrate; and
 (v) a molecular weight of about 230,000±10,000 Dalton as determined by molecular sieve chromatography;
and MBase has the following characteristics:
 (i) the ability to cleave phosphoglycolipid antibiotics at the phospholipid linkage;
 (ii) a pH optimum of greater than 5.7, and
 (iii) a temperature optimum of less than 37° C.

2. The process as claimed in claim 1, wherein the glycine/NaOH buffer has the pH 8.0-8.5.

3. The process as claimed in claim 1, wherein the filtrate of the biomass is extracted with ethyl acetate and then with acetone, and the biomass itself is extracted by stirring with acetone.

4. The process as claimed in claim 3, wherein the filtrate of the biomass and the biomass itself are mixed with acetone in a ratio of 1:0.3 by volume.

5. The process as claimed in claim 1, wherein the enzymatic degradation is performed with moenomycinase and MBase.

6. The process according to claim 5, wherein the enzymatic degradation takes place with lyophilized cells of Bacillus sp. DSM 4675 or the mutants or variants thereof.

7. The process as claimed in claim 1, wherein the enzymatic degradation is performed with moenmycinase and phosphatase.

8. The process as claimed in claim 6, wherein the culture medium for Bacillus sp. DSM 4675 is optimized with respect to the titers of moenomycinase and MBase by addition of phosphate.

9. The process as claimed in claim 7 wherein acid phosphatase or alkaline phosphates is employed as the phosphatase.

10. The process as claimed in claim 9, wherein the acid phsophatase from potato is employed.

11. The process as claimed in claim 9, wherein the alkaline phsophatase from calf intestine is employed.

12. The process as claimed in claim 8, wherein the phosphate is added in a concentration of 50-100 mM to the buffer.

* * * * *